(12) United States Patent
Baum et al.

(10) Patent No.: US 10,238,597 B2
(45) Date of Patent: Mar. 26, 2019

(54) PROBIOTIC TREATMENT OF SKIN DISEASES, DISORDERS, AND INFECTIONS: FORMULATIONS, METHODS AND SYSTEMS

(71) Applicants: Marc M. Baum, Pasadena, CA (US); Janelle M. Baum, Los Angeles, CA (US)

(72) Inventors: Marc M. Baum, Pasadena, CA (US); Janelle M. Baum, Los Angeles, CA (US)

(73) Assignee: BEAUTY BIOLABS LLC, Monrovia, CA (US)

( * ) Notice: Subject to any disclaimer, the term of this patent is extended or adjusted under 35 U.S.C. 154(b) by 0 days.

(21) Appl. No.: 15/354,359

(22) Filed: Nov. 17, 2016

(65) Prior Publication Data

US 2017/0143621 A1    May 25, 2017

Related U.S. Application Data

(60) Provisional application No. 62/257,615, filed on Nov. 19, 2015.

(51) Int. Cl.
| | |
|---|---|
| A61K 8/99 | (2017.01) |
| A61K 8/34 | (2006.01) |
| A61K 8/36 | (2006.01) |
| A61K 8/365 | (2006.01) |
| A61K 8/37 | (2006.01) |
| A61K 8/60 | (2006.01) |
| A61K 8/73 | (2006.01) |
| A61K 8/891 | (2006.01) |
| A61Q 5/00 | (2006.01) |

(52) U.S. Cl.
CPC ............... *A61K 8/99* (2013.01); *A61K 8/342* (2013.01); *A61K 8/345* (2013.01); *A61K 8/36* (2013.01); *A61K 8/365* (2013.01); *A61K 8/37* (2013.01); *A61K 8/60* (2013.01); *A61K 8/73* (2013.01); *A61K 8/891* (2013.01); *A61Q 5/006* (2013.01); *A61K 2800/884* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 4,090,522 A | 5/1978 | Donley et al. | |
| 4,568,343 A | 2/1986 | Leeper et al. | |
| 5,783,202 A | 7/1998 | Tomlinson et al. | |
| 6,244,273 B1 | 6/2001 | Higgins | |
| 6,582,695 B2 * | 6/2003 | Cavaliere Vesely | A61K 8/66 424/93.44 |
| 7,807,440 B2 * | 10/2010 | Molin | A23C 9/123 435/252.1 |
| 8,394,361 B1 * | 3/2013 | Frantz | A61K 8/044 424/70.1 |
| 8,574,561 B1 | 11/2013 | Patel et al. | |
| 8,673,277 B2 * | 3/2014 | Tamareselvy | A61K 8/025 424/70.16 |
| 9,265,719 B2 * | 2/2016 | Castiel | A61K 8/0216 |
| 2002/0168327 A1 | 11/2002 | Bailey et al. | |
| 2005/0031570 A1 * | 2/2005 | Grit | A61K 8/68 424/70.31 |
| 2009/0060962 A1 | 3/2009 | Castiel et al. | |
| 2010/0272839 A1 | 10/2010 | Gueniche et al. | |

FOREIGN PATENT DOCUMENTS

| | | |
|---|---|---|
| WO | WO-1994/000098 A1 | 1/1994 |
| WO | WO-1994/000109 A1 | 1/1994 |
| WO | WO-2015/026235 A2 | 2/2015 |

OTHER PUBLICATIONS

HubPages.com "10 best ways to get rid of dandruff naturally", published/updated Aug. 7, 2014 on page http://hubpages.coom./health/10-best-ways-to-get-rid-of-dandruff-naturally, retrieved Jan. 25, 2017.*
ATCC Tech Bulletin, ATCC Connection 2003, pp. 1-3.*
Bouslimani et al., Molecular Cartography of the Human Skin Surface in 3D. *Proc. Nat. Acad. Sci.*, 112:E2120-9 (2015).
Clavaud et al., Dandruff is Associated with Disequilibrium in the Proportion of the Major Bacterial and Fungal Populations Colonizing the Scalp. *PLoS One*, 8:e58203 (2013).
Costello et al., Bacterial Community Variation in Human Body Habitats Across Space and Time. *Science*, 326:1694-7 (2009).
Findley et al., The Skin Microbiome: A Focus on Pathogens and Their Association with Skin Disease. *PLoS Pathog.*, 10 (2014).
Fredricks et al., Molecular Identification of Bacteria Associated with Bacterial Vaginosis. *N. Engl. J. Med.*, 353:1899-11 (2005).
Gajer et a., Temporal Dynamics of the Human Vaginal Microbiota. *Sci. Transl. Med.*, 4:132ra152 (2012).
Grice et al., Nisc Comparative Sequencing Program, Topographical and Temporal Diversity of the Human Skin Microbiome. *Science*, 324:1190-2 (2009).
Gupta et al., Skin Diseases Associated with Malassezia species. *J. Am. Acad. Dermatol,.* 51:785-98 (2004).
Harding et al., Dandruff: a Condition Characterized by Decreased Levels of Intercellular Lipids in Scalp Stratum Corneum and Impaired Barrier Function. *Arch. Dermatol. Res.*, 294:221-23 (2002).
Hillier, The Complexity of Microbial Diversity in Bacterial Vaginosis. *N. Engl. J. Med.*, 353:1886-7 (2005).

(Continued)

*Primary Examiner* — Vera Afremova
(74) *Attorney, Agent, or Firm* — Marshall, Gerstein & Borun LLP

(57) ABSTRACT

The present invention teaches compositions, methods and kits for treating skin conditions, including dandruff. In various embodiments, the compositions include an effective amount of one or more probiotic microorganism of vaginal origin and/or a fraction thereof and/or a component of the metabolome for preventing and/or treating skin disorders of the scalp.

15 Claims, No Drawings

(56) References Cited

OTHER PUBLICATIONS

Nakatsuji et al., The Microbiome Extends to Subepidermal Compartments of Normal Skin. *Nat. Commun.*, 4 (2013).
Peterson et al., The NIH Human Microbiome Project. *Genome Res.*, 19:2317-23 (2009).
Ravel et al., Vaginal Microbiome of Reproductive-age Women. *Proc. Natl. Acad. Sci. U.S.A.*, 108:4680-7 (2011).
Reid et al., Potential Uses of Probiotics in Clinical Practice. *Clin. Microbiol. Rev.*, 16:658 (2003).
Remington: The Science and Practice of Pharmacy. 21st ed. Lippincott Williams & Wilkins: Philadelphia, 2005.
Rose et al., Commensal Bacteria Modulate Innate Immune Responses of Vaginal Epithelial Cell Multilayer Cutures. *PLoS One*, 7:e32728 (2012).
Schommer et al., Structure and Function of the Human Skin Microbiome. *Trends Microbiol.*, 21:660-8 (2013).
Soares et al., Malassezia Intra-Specific Diversity and Potentially New Species in the Skin Microbiota from Brazilian Healthy Subjects and Seborrheic Dermatitis Patients. *PLoS One*, 10:e0117921 (2015).
Srinivasan et al., Bacterial Communities in Women with Bacterial Vaginosis: High Resolution Phylogenetic Analyses Reveal Relationships of Microbiota to Clinical Criteria. *PLoS One*, 7:e37818 (2012).
Srinivasan et al., Temporal Variability of Human Vaginal Bacteria and Relationship with Bacterial Vaginosis. *PLoS One*, 5:e10197 (2010).
Turnbaugh et al., The Human Microbiome Project. *Nature*, 449:804-10 (2007).
Wang et al., Characterization of the Major Bacterial-fungal Populations Colonizing Dandruff Scalps in Shanghai, China, Shows Microbial Disequilibrium. *Exp. Dermatol.*, 24:398-400 (2015).
Xu et al., Dandruff-associated Malassezia Genomes Reveal Convergent and Divergent Virulence Traits Shared with Plant and Human Fungal Pathogens. *Proc. Natl. Acad. Sci. U.S.A.*, 104:18730-35 (2007).
International Search Report and Written Opinion of the International Searching Authority, PCT/US2016/062480, United States Patent Office dated Feb. 1, 2017.

* cited by examiner

PROBIOTIC TREATMENT OF SKIN DISEASES, DISORDERS, AND INFECTIONS: FORMULATIONS, METHODS AND SYSTEMS

CROSS-REFERENCE TO RELATED APPLICATION

This application claims priority to U.S. Provisional Application No. 62/257,615, filed on Nov. 19, 2015, the content of which is herein incorporated by reference in its entirety.

FIELD OF INVENTION

The present invention generally relates to new formulations for the prevention and/or treatment of skin disorders, diseases, and infections. In some embodiments, the present invention relates to dandruff and related disorders of the scalp. In some embodiments, the present invention is also directed towards novel cosmetic compositions and processes for preventing and/or treating dandruff and related conditions of the scalp. In certain embodiments, the present invention also relates to assemblies or kits that are suitable for use in conjunction with one or more method and/or composition of the invention. The present invention also relates to the field of oral and topical products for scalp care.

BACKGROUND

All publications referenced herein are incorporated by reference to the same extent as if each publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The Human Microbiome Project (HMP) is improving our understanding of the dynamics of microbiota in healthy individuals, and the pathogenic capabilities of key species that mediate poor health outcomes (1,2). Understanding the molecular mechanisms that mediate symbiosis between commensal bacteria and humans may redefine how we view the evolution of adaptive immunity and consequently how we approach the treatment of numerous immunologic disorders. The skin is one of five anatomic locations studied as part of the HMP. The molecular composition of this organ is derived from host cells, microbiota, and external molecules. The chemical makeup of the skin surface is largely undefined. Recently, Bouslimania et al. developed 3D maps revealing that the molecular composition of skin has diverse distributions and that the composition is defined not only by skin cells and microbes but also by daily routines, including the application of hygiene products (3).

The composition of the human skin microbiota has been correlated with skin anatomy, dividing into moist, dry, and sebaceous microenvironments, and can be influenced by beauty and hygiene (3). The skin is our first line of defense against foreign invaders and is also home to a diverse population of microbes. The majority of these microbes are commensal (nonpathogenic permanent residents) or transient (temporary residents) organisms. In pathogenic interactions, only the microbe benefits, while the host is eventually harmed. Many skin pathogens can be typically found living on the skin as commensal organisms, but microbial dysbiosis (or microbial imbalance), host genetic variation, and immune status may drive the transition from commensal to pathogen (4).

Analysis of bacterial diversity on human skin employing 16S rRNA gene sequencing revealed that multiple skin sites exhibited greater bacterial diversity than in the gut and oral cavity; interpersonal variation varied significantly within the population studied, and the temporal stability of the analyzed skin microbial communities remained relatively stable (5). Physiological characteristics of various skin sites are associated with different levels of bacterial diversity (6). Spatially, the skin microbiota may extend to subepidermal compartments (7). Regions such as the face, chest, and back, areas with a high density of sebaceous glands, promote growth of lipophilic microorganisms such as *Propionibacterium* and *Malassezia*.

It is postulated that the predominant fungus of the skin microbiota, *Malassezia*, is involved in seborrhoeic dermatitis. This chronic inflammatory skin disorder is often first diagnosed around puberty and is caused by an increase in cutaneous lipids resulting from androgen-driven sebaceous gland development and sebum secretion (8). The disease also often occurs in patients older than 50 years. Dandruff is the common term for seborrhea of the scalp. It is mainly associated with *M. restricta* and *M. globosa* (9,10), and has a very high prevalence of nearly 50% of the population (8). Improvements in the disease can be achieved by therapeutic application of antifungal, but not antibacterial agents. The mechanisms underlying pathogenicity are incompletely understood. Impaired skin barrier function facilitates the course of the disease (11). The fungus secretes a lipase that splits triglycerides into irritant fatty acids that may induce hyperproliferation and scaling, or releases arachidonic acid, which is also involved in inflammation (12). From the current literature it can be speculated that the fungus, which is part of the normal skin microbiota, switches to a pathogenic state when its growth is not controlled. What these control factors are and how they are dampened are not yet understood.

SUMMARY OF THE INVENTION

In some embodiments, the invention teaches a method for treating skin disorders, diseases, and infections including by administering formulations topically and/or orally. In some embodiments, the formulations contain: one or more probiotic microorganisms isolated from the vagina of mammals, including humans; and/or one or more soluble components of the metabolome; and/or cell lysate from said probiotic microorganisms; and/or other functional additives described herein. In some embodiments, the invention teaches the aforementioned formulations used in the methods.

In some embodiments, the probiotic formulation contains one or more ingredients from one or more of the following groups: solubilizers and permeation enhancers; anti-seborrhoeic agents; skin hydrating agents; skin conditioning agents; antimicrobial agents; irritation-mitigating additives; natural functional additives; and botanical additives.

In some embodiments, the method further describes novel methods for applying one or more of the topical probiotic formulations to the scalp. In some embodiments, the invention further teaches applicator devices and kits for product application to the scalp.

Provided herein are compositions comprising one or more probiotic microorganisms and/or one or more soluble metabolome components and/or one or more cell lysate components.

In some embodiments, the composition is formulated for oral administration. In some embodiments, the composition is formulated for topical administration. In additional embodiments, the composition is formulated for topical administration to the skin. In one embodiment, the composition is formulated to treat dandruff.

In various embodiments, the probiotic microorganisms in the composition comprise one or more bacterial species isolated from human clinical vaginal specimen. In exemplary embodiments, the probiotic comprises one or more bacterial species selected from the group consisting of: Lachnospiraceae, *Ruminococcaceae; Acidovorax, Aerococcus, Atopobium, Cloacibacterium, Corynebacterium, Dialister, Eggerthella, Enterococcus, Escherichia, Gardnerella, Haemophilus, Lactobacillus, Leptotrichia, Megasphaera, Mobiluncus, Mycoplasma, Neiseria, Parvimonas, Peptoniphilus, Peptostreptococcus, Prevotella, Sneathia, Staphylococcus, Streptococcus, Ureaplasma*, and *Veillonella*.

In some embodiments, the metabolome component comprises one or more short chain fatty acids. In exemplary embodiments, the soluble metabolome component comprises one or more substances selected from the group consisting of: formic acid, acetic acid, propanoic acid, butanoic acid (butyric acid), ethanedioic acid, propanedioic acid, butanedioic acid, cis-butenedioic acid (maleic acid), trans-butenedioic acid (fumaric acid), pentanedioic acid, hexanedioic acid, and lactic acid. In some embodiments, the lactic acid is DL-lactic acid, D-lactic acid, L-lactic acid or combinations thereof.

Also provided herein is a method for treating skin disorders, diseases, and infections, comprising administering a composition comprising one or more probiotic and/or one or more soluble metabolome components and/or one or more cell lysate components to a subject in need thereof. In one embodiment, the skin disorder is dandruff. In exemplary embodiments of the method, the composition may be administered orally, topically, to the subject's scalp or combinations thereof.

In various embodiments of the method, the probiotic comprises one or more bacterial species isolated from human clinical vaginal specimen. In exemplary embodiments, the probiotic comprises one or more bacterium selected from the group consisting of: Lachnospiraceae, *Ruminococcaceae; Acidovorax, Aerococcus, Atopobium, Cloacibacterium, Corynebacterium, Dialister, Eggerthella, Enterococcus, Escherichia, Gardnerella, Haemophilus, Lactobacillus, Leptotrichia, Megasphaera, Mobiluncus, Mycoplasma, Neiseria, Parvimonas, Peptoniphilus, Peptostreptococcus, Prevotella, Sneathia, Staphylococcus, Streptococcus, Ureaplasma*, and *Veillonella*.

In some embodiments of the methods described herein, the soluble metabolome component comprises one or more short chain fatty acids. In exemplary embodiments, the soluble metabolome component comprise one or more substances selected from the group consisting of: formic acid, acetic acid, propanoic acid, butanoic acid (butyric acid), ethanedioic acid, propanedioic acid, butanedioic acid, cis-butenedioic acid (maleic acid), trans-butenedioic acid (fumaric acid), pentanedioic acid, hexanedioic acid, and lactic acid. In some embodiments, the lactic acid is DL-lactic acid, D-lactic acid, L-lactic acid or combinations thereof.

Further provided herein is a kit, comprising the compositions described herein and instructions for the use thereof to treat a skin condition. In some embodiments, the kit further comprises one or more applicator configured to apply the composition.

Also provided herein is a method for reducing dandruff of the scalp in a subject in need thereof, comprising administering to the subject an effective amount of a composition that comprises, consists of or consists essentially of one or more *Lactobacillus* spp. isolated from human clinical vaginal specimens; one or more of D,L-lactic acid, L-lactic acid, or D-lactic acid; and one or more cell lysate components of the *Lactobacillus* spp., so as to reduce dandruff in the subject. In some embodiments, the *Lactobacillus* spp. have undergone less than 6 subcultures. In some embodiments, the *Lactobacillus* spp. reduces or inhibits the growth of *Malassezia* spp. In some embodiments, the composition further comprises butyric acid. In one embodiment, the composition is administered orally. In another embodiment, the composition is administered topically. In a further embodiment, the composition is administered to the subject's scalp. In some embodiments, the composition further comprises butyric acid, glucose and glycogen. In a further embodiment, the composition further comprises butyric acid, glucose, glycogen, magnesium ascorbyl phosphate, cetyl alcohol, dimethicone, isopropyl myristate and glycerol. In an additional embodiment, the composition comprises butyric acid, glucose, glycogen, magnesium ascorbyl phosphate, propylene glycol, Quaternium-52 and ethanol. In exemplary embodiments, the pH of the composition is between 3 and 6. In some embodiments, the pH is between 4 and 6. In further embodiments, the pH is between 3 and 5. In additional embodiments, the pH is between 5 and 6. In some embodiments, the methods further comprise administering one or more anti-seborrhoeic agents. In one embodiment, the compositions described herein and the anti-seborrhoeic agents are administered sequentially. In another embodiment, the composition described herein and the anti-seborrhoeic agents are administered simultaneously.

In some embodiments, the reduction or inhibition of the growth of *Malassezia* spp. is assessed using scalp and/or vaginal tissue culture methods that would be apparent to a person of skill in the art. The tissue culture methods comprise using human cell lines such as human skin equivalent cell culture models such as EpiDermFT™, MatTek Corporation, Ashland, Mass. and vaginal epithelial cell culture models, such as EpiVaginal™, MatTek Corporation.

Also provided herein is a business method for operating a salon in which dandruff of the scalp is reduced in a subject. The method includes providing a subject in a salon, providing a hair care specialist in the salon and administering to the subject an effective amount of a composition comprising one or more probiotic microorganisms and/or one or more soluble metabolome components and/or one or more cell lysate components, as described herein, wherein the composition is administered by the hair care specialist.

Further provided herein is a business method for operating a salon in which dandruff of the scalp is reduced in a subject. The method includes providing a subject in a salon, providing a hair care specialist in the salon and administering to the subject an effective amount of a composition comprising one or more *Lactobacillus* spp. isolated from human clinical vaginal specimens, one or more of D,L-lactic acid, L-lactic acid, or D-lactic acid and one or more cell lysate components of the *Lactobacillus* spp., wherein the composition is administered by the hair care specialist.

Also provided herein is a business method for distributing a composition for the reduction of dandruff of the scalp in one or more subjects, said composition for use by the one or more subjects in their homes. The method includes providing the one or more subjects and distributing to the one or more subjects an effective amount of a composition comprising one or more probiotic microorganisms and/or one or more soluble metabolome components and/or one or more cell lysate components, as described herein.

Also provided herein is a business method for distributing a composition for the reduction of dandruff of the scalp in one or more subjects, said composition for use by the one or more subjects in their homes. The method includes providing the one or more subjects and distributing to the one or more subjects an effective amount of a composition comprising one or more *Lactobacillus* spp. isolated from human clinical vaginal specimens, one or more of D,L-lactic acid, L-lactic acid, or D-lactic acid and one or more cell lysate components of the *Lactobacillus* spp.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure.* $5^{th}$ ed., J. Wiley & Sons (New York, N.Y. 2001); *International Cosmetic Ingredient Dictionary and Handbook.* 9th ed.; Cosmetic, Toiletry, and Fragrance Association: Washington DC, 2002; Vol. 1-3; 2001 *McCutcheon's Directories.* McCutcheon's Division, The Manufacturing Confectioner Publishing Co.: Glen Rock, N.J., 2001; Vol. 1-2; DiBerardino, L., *CBR Cosmetic Bench Reference—Directory of Cosmetic Ingredients* 2005. Cosmetics and Toiletries, Allured Publishing Corporation: Carol Stream, Ill., 2005; and *Remington: The Science and Practice of Pharmacy.* 21st ed.; Lippincott Williams & Wilkins: Philadelphia, 2005, together provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For the purposes of the present invention, the following terms are defined below.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Other definitions of terms may appear throughout the specification. Before the exemplary embodiments are described in more detail, it is to understand that this disclosure is not limited to particular embodiments described. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. The publications discussed herein are provided solely for their disclosure prior to the filing date of the present application. Nothing herein is to be construed as an admission that such publications constitute prior art to the claims appended hereto.

It will be understood that in the following, preferred embodiments referred to in relation to one broad aspect of the invention are equally applicable to each of the other broad aspects of the present invention described above. It will be further understood that, unless the context dictates otherwise, the preferred embodiments described below may be combined.

When used herein, the term "topical" includes references to formulations that are configured for application to body surfaces (e.g., the skin or mucous membranes). Applicable mucous membranes include, but are in no way limited to, the mucosa of the vagina, the penis, the urethra, the bladder, the anus, the mouth (including the mucosa of the cheek, the soft palate, the under surface of tongue and the floor of the mouth), the nose, the throat (including the mucosa of the pharynx, the larynx, the trachea and the esophagus), the bronchi, the lungs, the eye, and the ear.

With the foregoing background in mind, certain embodiments of the present invention are based on one or more of the observations that: (1) Clinical microbial isolates from the human vaginal microbiome can be effective at regulating the skin microbiome, thereby preventing dysbiosis; (2) Unexpectedly, the above vaginal microbial isolates rapidly lose key aspects of their functional metagenomic potential following sub-culturing. For an effective, consistent probiotic product, the cultured organism is preferably closely related (i.e., small number of subcultures) to the mother culture; (3) The vaginal microbiome can contain a high diversity of organisms, making the rational selection of probiotic candidates for the treatment of skin disorders, diseases, and infections challenging. A novel screening system that is not obvious to one who is well-versed in the art; (4) Soluble components of the metabolome can complement the efficacy of an oral or topical probiotic formulation for the treatment of skin disorders, diseases, and infections. These metabolites encompass compounds produced by complex microbial communities in various body habitats, as well as compounds produced by the human host; Other formulation additives, either synthetic or naturally derived, can enhance product efficacy; (5) Novel topical product application strategies can enhance product efficacy and adherence; (6) Novel topical product application devices can enhance product efficacy and adherence.

Probiotic Microorganism(s)

Probiotics are defined as "live microorganisms which when administered in adequate amounts confer a health benefit on the host" (13). Aside from some isolated successes, probiotics largely have failed to consistently live up to their obvious theoretical promise for the treatment of human diseases and disorders. Skin disorders, diseases, and infections have been linked to a microbial dysbiosis. In the context of the human scalp, rudimentary culture-independent studies using clone library sequencing of phylogenetically informative genes have failed to significantly advance our understanding of the etiology of seborrhoeic dermatitis (i.e., dandruff) (10, 14, 15). Dandruff appears to be the result of a dysbiosis of the scalp microbiome, prompting some experts in the art to propose the use of probiotics for treatment.

Many of the probiotic organisms disclosed in the art are obtained from established culture libraries where the history and even origin of the organism is often unknown. Other probiotic organisms are commonly enteric in origin. In the present invention, a novel, non-obvious approach is disclosed, which is based on the observation that members of the vaginal microbiome, preferably, but not limited to the human microbiome, can be effective probiotic agents for the treatment of skin disorders, diseases, and infections. The normal vaginal microbiota make up a complex, diverse community believed to play an important protective role in maintaining the woman's health (16). In the present invention, the probiotic organisms are isolated directly from clinical vaginal specimens. In some embodiments of the invention, the clinical specimens are obtained and preserved using standard methods from the human vaginal tract. In another embodiment of the invention, the specimens are obtained and preserved using standard methods from the vaginal tract of a nonhuman, mammalian animal model including, but not limited to: non-human primates (e.g., macaques, baboons, chimpanzees); members of the Bovidae (e.g., sheep and goats); members of the Suidae (e.g., pigs, mini-pigs); and rodents (e.g., guinea pigs, mice, and rats). Axenic (i.e., single species/genus) cultures of candidate probiotic organisms are isolated from these specimens using microbiological methods known in the art.

Surprisingly, it has been observed that microbial isolates from vaginal specimens can rapidly lose key aspects of the functional metagenomic potential following sub-culturing. This observation has not been recognized by the art in the development of probiotic products. In some embodiments of the present invention, the subculturing of the vaginal isolates is minimized. In certain embodiments, the cultured organism is 24-1, 20-2, 16-3, 12-4, 8-6, 4, or fewer generations (i.e., passages) removed from the mother culture.

The vaginal microbiome can contain a high diversity of organisms (17-21). The rational development of probiotic candidates for the treatment of skin disorders, diseases, and infections therefore requires a systematic screening system. Therefore, in some embodiments, the present invention discloses a novel, high-throughput screening system for the isolation of vaginal microbiota that is not obvious to one who is well-versed in the art. First, the organisms must be cultivatable in pure culture without economically and practically prohibitive requirements. Second, the organisms must be viable at a pH below the natural, normal pH of skin (ca. 5.5). In certain embodiments of the disclosed invention, selection of candidate probiotics is predicated by their ability to grow in co-cultures with *Malassezia* spp. In some embodiments of the disclosed invention, selection of candidate probiotics is predicated by their ability to outcompete *Malassezia* spp. in co-cultures. In some embodiments of the invention, the probiotic isolate is screened in a cell culture model using human-derived cells. In certain embodiments, this screening is based on signaling between the microorganism and the human cells, where signaling is a measure of antagonistic (e.g., eliciting a detrimental response such as inflammation and the production of chemokines and cytokines by the human-derived cells) or beneficial effects (e.g., producing an anti-inflammatory effect on the human-derived cells). In certain embodiments, the cell culture model is based on immortalized vaginal epithelial cells such as described by Rose at al. (22), which is hereby incorporated herein by reference in its entirety as though fully set forth. In certain embodiments of the disclosed invention, the above co-culture experiments are carried out in a high throughput, 96-well or 384-well plate format, or the like.

Probiotic, vaginally derived bacteria suitable for use in the present invention include, but are not limited to members from the following bacterial families: Lachnospiraceae and/or *Ruminococcaceae*; and/or members from the following bacterial genera: *Acidovorax, Aerococcus, Atopobium, Cloacibacterium, Corynebacterium, Dialister, Eggerthella, Enterococcus, Escherichia, Gardnerella, Haemophilus, Lactobacillus, Leptotrichia, Megasphaera, Mobiluncus, Mycoplasma, Neiseria, Parvimonas, Peptoniphilus, Peptostreptococcus, Prevotella, Sneathia, Staphylococcus, Streptococcus, Ureaplasma*, and/or *Veillonella*.

In certain embodiments, the probiotic bacteria for use according to the present invention comprises, consists of, or consists essentially of at least one lactic acid-producing bacteria. In certain embodiments, one or more probiotic bacteria are selected from the genus *Lactobacillus*, including, but not limited to commensal vaginal *Lactobacillus* species such as *L. crispatus, L. fermentum, L. gasseri, L. iners, L. jensenii, L. reuteri, L. rhamnosus*, and *L. vaginalis*.

The microorganism(s) may be included in a composition according to the invention in a live, semi-active or inactivated, or dead form.

Soluble Metabolome Component

It is increasingly becoming recognized in the art that the human metabolome, i.e., small molecule metabolites found in the human body, can be implicated in disease. However, an unexpected observation disclosed in the present application, and upon which certain embodiments of the present invention are based, is that metabolites produced by complex microbial communities in various body habitats, as well as produced by the human host can complement the efficacy of an oral or topical probiotic formulation for the treatment of skin disorders, diseases, and infections. As used herein, the term "soluble metabolome component" refers to a metabolite or metabolites identified in the human microbiome, including, but not limited to the vaginal microbiome. Said soluble metabolome component can be produced by one or more bacterial taxa identified in the human microbiome, one or more fungal taxa identified in the human microbiome, or by host (e.g. human or other animal described herein) cells.

In some embodiments, one or more soluble metabolome components that may be included in the inventive compositions and kits, and used in conjunction with the inventive methods described herein include, but are not limited to one or more short chain fatty acids. In some embodiments, the short chain fatty acids may include, but are in no way limited to one or more of: formic acid, acetic acid, propanoic acid, butanoic acid (butyric acid), ethanedioic acid, propanedioic acid, butanedioic acid, cis-butenedioic acid (maleic acid), trans-butenedioic acid (fumaric acid), pentanedioic acid, and hexanedioic acid. In certain embodiments, one or more soluble metabolome components disclosed in the present invention may include one or more of α-hydroxy carboxylic acids (e.g., glycolic acid, lactic acid, malic acid, citric acid, tartaric acid, 2-hydroxy-iso-valeric acid, and mandelic acid) and β-hydroxy carboxylic acids (e.g., β-hydroxybutyric acid, salicylic acid, and carnitine). In certain embodiments of the disclosed invention, racemic or enantiomerically pure (>90% ee) forms of the above acids are used. Merely by way of example, DL-lactic acid, D-lactic acid, and/or L-lactic acid can be used. In certain embodiments of the invention, lactide dimers, represented by the formula:

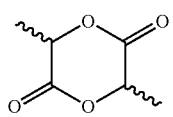

derived from the above-described monomers are used in the formulation.

In some embodiments, one or more soluble metabolome components that can be included in the inventive formulations described herein include, but are not limited to: natural amino acids, simple sugars and sugar alcohols (e.g., fucose, fructose, glucose, arabitol, ribose, sucrose, mannitol, galactose, threitol, maltotriose, maltose, maltotetraose), glucosamine, glucose oligosaccharides (e.g., maltotriose, maltotetraose, maltopentaose, and maltohexaose), 1-acetoxy-2-propanol, 1-hydroxy-2-propanone, 1-methyl-β-galactopyranoside, 1,2-propanediol, 1,2-propanediol-2-acetate, 1,3-dihydro-iso-benzofuran, 1,4-dimethyldioxane, 2-aminoethylphosphate, 2-ethyl-4-methyl-1,3-dioxolane, 2-hydroxy-γ-butyrolactone, 2-methylebnzoic acid, 2-o-glycerol-β-galactopyranoside, 2(5H)-furanone, 3-pyridinecarboxamide, 9-octadecenoic acid, α-tocopherolacetic acid, butyrolactone, cyclopentanol, diethylene glycol, ethanolamine, galactofuranose, galactopyranose, gluconic acid-1,5-lactone, glucopyranose, glycogen, heptadecanoic acid, homoserine, 2,3-hydroxypropyl-2-aminoethyl phosphate, 2-methyl-2-hydroxybutanoic acid, octadecanoic acid, cis-11-octadecanoic acid, octadecanol, palmitic acid, pentadecanoic acid, pyroglutamic acid, pyruvic acid, sialic acid, ribose-5-phosphate, tetradecanoic acid, triethanolamine, tyramine, butylamine, hydroxylamine, N-acetylneuraminate, N-acetylornithine, alanylisoleucine, guanine, isoleucyl-iso-leucine, 1-oleoylglycerophosphoserine, trans-4-hydroxyproline, 12-hydroxyeicosatetraenoic acid (12-HETE), deoxycarnitine, carnitine, acyl-carnitines (e.g., acetylcarnitine), propionylcarnitine, and butyrylcarnitine), N-acetylmethionine phenyllactate, 3-(4-hydroxyphenyl)lactate, palmitoyl, sphingomyelin oleate (18:1n9), eicosenoate (20:1n9 or 11), dihomo-linoleate (20:2n6), linoleate (18:2n6), dihomo-linolenate (20:3n3 or n6), arachidonate (20:4n6), uridine, myo-inositol, 5-oxoproline, glycerol 3-phosphate (G3P), 1-oleoylglycerophosphoethanolamine, hypoxanthine, phenylacetylglutamine, p-cresol, urea, N-acetylglutamate, N-acetylaspartate (NAA), nicotinate, 2-hydroxystearate, α-hydroxyisocaproate, 2-aminobutyrate, 13-HODE, uracil, 2-hydroxyglutarate, sphingosine, sphinganine, glutathione, reduced (GSH), glycerophosphorylcholine (GPC), alanylleucine, alanylphenylalanine, alanylvaline, glycylleucine, glycylproline, threonine, threonylphenylalanine, valinylglutamate, ornithine, thymine, N-acetylputrescine, pipecolate, agmatine, 5-aminovalerate, 1-phenylethylamine, sphingomyelin, N-acetylmethionine oleate (18:1n9), phenyllactate (PLA), oleate (18:1n9), and N-acetylmethionine.

In the context of the invention, the term "soluble metabolome component" can also refer to a metabolite or metabolites present in the supernatant of a microbial culture from which the probiotic cells have been removed. Said culture can be axenic (i.e., contains only one microbial species) or polymicrobial. In some embodiments, the culture is grown to a cell density of at least about $OD_{500}$ 0.1-0.9, or 0.2-0.8, 0.3-0.7, or 04.-0.6, or 0.5. In certain embodiments, the culture is grown to a cell density of at least 0.5. In certain embodiments, the cells are removed by centrifugation. In some embodiments, the supernatant is filtered. In some embodiments, the supernatant may be used directly in the formulations of the present invention. In certain embodiments, one or more of the metabolites may be isolated from the supernatant by any suitable means prior to use.

Cell Lysate

As used herein, the term "cell lysate" or "lysate" refers to probiotic cells that have been lysed by any suitable means. In some embodiments, the cell debris is removed prior to use. In certain embodiments the cell lysates are filtered prior to use. Merely by way of non-limiting examples, cells can be lysed by sonication, homogenization, shearing, or chemical lysis.

The microorganism(s) included in the inventive formulations described herein may also be included in the form of fractions of cell components or in the form of metabolites. The microorganism(s), soluble metabolome component(s), or lysate(s) may also be introduced in the form of a lyophilized powder, a culture supernatant and/or, where appropriate, in a concentrated form.

In certain embodiments of the present invention, the probiotic bacteria, soluble metabolome component and/or cell lysate is formulated for administration to the skin and/or orally.

It is understood that the formulation for use in the present invention may comprise, consist of, or consist essentially of one or more of: a probiotic bacterium and/or at least one soluble metabolome component and/or at least one cell lysate of a probiotic bacteria described herein. It will be further understood that the formulation may comprise, consist of, or consist essentially of more than one probiotic bacteria, soluble metabolome component, and/or cell lysate. For example, the formulation may comprise 0, 1, 2, 3, 4, 5, 6, 7, 8, 9, 10, 11, 12, 13, 14, 15, 16, 17, 18, 19, 20 or more different probiotic bacteria and/or 0, 1, 2, 3, 4, 5, 6, 7, 8, 9, 10, 11, 12, 13, 14, 15, 16, 17, 18, 19, 20 or more different soluble metabolome components, and/or 0, 1, 2, 3, 4, 5, 6, 7, 8, 9, 10, 11, 12, 13, 14, 15, 16, 17, 18, 19, 20 or more cell lysates. It will be understood by the skilled person that as used herein the term probiotic refers to a live microorganism, including bacteria or fungi for example, which, when orally or topically applied in sufficient numbers, beneficially affects the host organism, i.e., by conferring one or more demonstrable health benefits on the host organism.

It will also be readily apparent that the formulations of the present invention may further include one or more probiotics. Whilst there are no lower or upper limits for probiotic use, it has been suggested that at least $10^4$-$10^{13}$, at least $10^6$-$10^{10}$, or at least $10^8$-$10^{11}$, colony forming units (CFUs) as a daily dose will be effective to achieve the beneficial health effects in a subject. Administration of the probiotic(s) is oral and/or topically in formulations described in detail below.

Oral Formulation

A microorganism described herein and/or a fraction thereof and/or a soluble metabolome component thereof, may moreover be formulated with the usual excipients and components for such oral compositions or food supplements, i.e., in particular fatty and/or aqueous components, humectants, thickeners, preservatives, texturing agents, flavor enhancers and/or coating agents, antioxidants, preservatives, and dyes that are customary in the food sector. The formulating agents and excipients for oral compositions, and in particular for food supplements, are known in the art and will not be the subject of a detailed description herein.

Milk, yogurt, cheese, fermented milks, milk-based fermented products, ice creams, cereal-based products or fermented cereal-based products, milk-based powders, infant and baby formulas, food products of confectionary, chocolate or cereal type, animal feed, in particular for domestic animals, tablets, gel capsules or lozenges, liquid bacterial suspensions, oral supplements in dry form and oral supplements in liquid form are especially suitable for use as dietetic or pharmaceutical supports.

According to one embodiment, a composition according to the invention administered orally, especially a first composition, may be formulated in the form of coated tablets, gel capsules, gels, emulsions, tablets, capsules, hydrogels, food bars, compact or loose powders, liquid suspensions or solutions, confectionery products, fermented milks, fermented cheeses, chewing gum, toothpaste or spray solutions, or food carriers. In the description and in the examples that follow, unless otherwise indicated, the percentages are percentages by weight and the ranges of values written in the form "between . . . and . . . " include the upper and lower limits specified. The ingredients are mixed, before being formulated, in the order and under conditions that can be readily determined by those skilled in the art. The content and the nature of the ingredients used in the compositions of the invention are adjusted by those skilled in the art in such a way as not to substantially affect the properties required for the compositions of the invention.

It will be further apparent that the formulation for use according to the present invention may comprise, consist of, or consist essentially of any pharmaceutically effective amount of one or more probiotic bacteria and/or one or more soluble metabolome component and/or one or more cell lysate, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, 30 about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0%, or more by weight of probiotic bacteria and/or soluble metabolome component and/or cell lysate.

In certain embodiments, the formulation for use according to the present invention may comprise, consist of, or consist essentially of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of probiotic bacteria and/or soluble metabolome component and/or cell lysate.

Topical Formulation

In certain embodiments of the present invention, the formulation further includes at least one of betaine and/or a polyol (e.g., xylitol or lactitol) and/or a polyphenol (e.g., epicatechin or gallocatechin). It will be understood that the disorder treated according to the inventive methods and by the inventive kits, devices and formulations may be any disorder associated with skin diseases, disorders, and/or infections. In certain embodiments, the disorder may include, but is in no way limited to seborrhoeic dermatitis (dandruff), psoriasis, acne, atopic dermatitis, dry skin, allergy, rashes, UV-irritated skin, detergent irritated skin (including irritation caused by enzymes used in washing detergents and sodium lauryl sulfate), thinning skin (e.g., skin from the elderly and children), combinations thereof, and the like.

In various embodiments, the topical formulation for use according to the present invention may comprise, consist of, or consist essentially of any pharmaceutically effective amount of the probiotic bacteria and/or soluble metabolome component and/or cell lysate, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, 30 about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of probiotic bacteria and/or soluble metabolome component and/or cell lysate.

In various embodiments, the topical formulation for use according to the present invention may comprise, consist of, or consist essentially of, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of probiotic bacteria and/or soluble metabolome component and/or cell lysate.

The topical formulation for use in the present invention may be in any form suitable for application to the body surface, such as a foam, shampoo, conditioner, mousse, cream, lotion, sprays, solution, gel, ointment, paste, plaster, paint, bioadhesive, suspensions or the like, and/or may be prepared so as to contain liposomes, micelles, and/or microspheres. Such a formulation may be used in combination with an occlusive over-layer so that moisture evaporating from the body surface is maintained within the formulation upon application to the body surface and thereafter.

Topical formulations include those in which the active ingredient(s) is (are) dissolved or dispersed in a dermatological vehicle known in the art (e.g., aqueous or non-aqueous gels, ointments, water-in-oil, or oil-in-water emulsions). Constituents of such vehicles may comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol, or glycerol), oils (e.g., a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components (e.g., when the formulation is an aqueous gel, components in addition to water) selected from the following list: a solubilizing agent or solvent (e.g., a 13-cyclodextrin, such as hydroxypropyl 13-cyclodextrin, or an alcohol or polyol such as ethanol, propylene glycol, or glycerol); a thickening agent (e.g., hydroxyethylcellulose, hydroxypropylcellulose, carboxymethylcellulose, or carbomer); a gelling agent (e.g., a polyoxyethylene-polyoxypropylene copolymer); a preservative (e.g., benzyl alcohol, benzalkonium chloride, chlorhexidine, chlorbutol, a benzoate, potassium sorbate, or EDTA or salt thereof); and pH buffering agent(s) (e.g., a mixture of dihydrogen phosphate and hydrogen phosphate salts, or a mixture of citric acid and a hydrogen phosphate salt).

In particular compositions: (i) Water may be present at from 55 to 75% (e.g., from 60 to 72.5%) by weight; (ii) The one or more polar, non-aqueous solvents may (together) be present at from 15 to 40% (e.g., from 24 to 35%) by weight; (iii) Glycerol, if used, may be present at from 5 to 25% (e.g., from 15 to 20%) by weight; (iv) Ethanol, if used, may be present at from 3 to 10% (e.g., from 5 to 8%) by weight; (v) Propylene glycol, if used, may be present at from 2 to 15% (e.g., from 4 to 6%) by weight; (vi) The preservative may be present at from 0.1 to 3% (e.g., about 1%) by weight; (vii) The thickening agent may be present at from 1 to 5% (e.g., about 2% by weight).

In further particular topical compositions, the pH buffering agent(s) may, if employed and when dissolved in the water component of the composition, provide a pH in the range of 1.5 to 8 (e.g. about pH 5.5). In one embodiment of the invention, the pH of the topical formulation is buffered to a value of 5.5, the natural, typical pH of skin. In one preferred embodiment of the invention, the topical formulation has a pH that is more acidic than normally found in natural human skin, in the range 1.5 to 5.0.

Methods of producing topical pharmaceutical compositions such as creams, ointments, lotions, sprays, shampoos, conditioners, and sterile aqueous solutions or suspensions are well known in the art.

A pharmaceutically acceptable carrier may also be incorporated in the formulation of the present invention and may be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

The term "pharmaceutically acceptable" or "pharmaceutically acceptable carrier" is used herein to refer to a compound or composition that may be incorporated into a pharmaceutical formulation without causing undesirable biological effects or unwanted interaction with other components of the formulation.

"Carriers" or "vehicles" as used herein refer to carrier materials suitable for incorporation in a topically applied composition. Carriers and vehicles useful herein include any such materials known in the art that are non-toxic and do not interact with other components of the formulation in which it is contained in a deleterious manner.

The term "aqueous" refers to a formulation that contains water or that becomes water-containing following application to the skin or mucosal tissue.

In various embodiments, the pharmaceutical formulation of the invention includes a pharmaceutically acceptable topical carrier and an active agent that comprises, consists of, or consists essentially of a probiotic bacteria and/or soluble metabolome component and/or a cell lysate of a probiotic bacteria. Formulations of the invention may optionally contain a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer.

A film former, when it dries, forms a protective film over the site of application. The film inhibits removal of the active ingredient and keeps it in contact with the site being treated. An example of a film former that is suitable for use in this invention is Flexible Collodion, USP. Collodions are ethyl ether/ethanol solutions containing pyroxylin (a nitrocellulose) that evaporate to leave a film of pyroxylin. A film former may act additionally as a carrier. Solutions that dry to form a film are sometimes referred to as "paints".

Creams, as is well known in the arts of pharmaceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type.

Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin (e.g., methylcellulose, sodium carboxymethyl-cellulose, or the like).

Solutions are homogeneous mixtures prepared by dissolving one or more chemical substances (solutes) in a liquid such that the molecules of the dissolved substance are dispersed among those of the solvent. The solution may contain other pharmaceutically or cosmetically acceptable chemicals to buffer, stabilize, or preserve the solute. Common examples of solvents used in preparing solutions are ethanol, water, propylene glycol, or any other acceptable vehicles.

As is well-known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules", i.e., gelling agents, are cross-linked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well-known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum). Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the formulations. Liposomal preparations herein include cationic (positively charged), anionic (negatively charged), and neutral preparations. Cationic liposomes are readily available. For example, N-[1,2,3-dioleyloxy)propyl]-N,N,N-triethyl-ammonium (DOTMA) liposomes are available under the tradename Lipofectin® (GIBCO BRL, Grand Island, N.Y.). Similarly, anionic and neutral liposomes are readily available, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

In certain embodiments of the invention, the topical product is applied as a mousse. Aerosolized mousses are well known in the art and are easy and safe to use. A typical example of a mousse formulation for application to the scalp has been described in U.S. Pat. No. 5,783,202 included herein by reference. The probiotic and/or soluble metabolome component and/or lysate and/or other product ingredient will be included at a concentration from about 0.1 to about 10% by weight, about 70 to about 97% by weight of a foaming agent, which is a quick breaking alcoholic foaming agent in one embodiment of the invention; and from about 3 to about 20% by weight of an aerosol propellant.

Micelles are known in the art as comprised of surfactant molecules arranged so that their polar head groups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol-10, and nonoxynol-30.

Microspheres, similarly, may be incorporated into the present formulations. Like liposomes and micelles, microspheres essentially encapsulate one or more components of the present formulations. They are generally although not necessarily formed from lipids, including charged lipids such as phospholipids, and/or polysaccharides. Preparation of microspheres is well known in the art.

Solubilizers and Permeation Enhancers

Various additives, known to those skilled in the art, may be included in the topical formulations. For example, solvents, including relatively small amounts of alcohol, may be used to solubilize certain formulation components. With particularly severe skin conditions it may be desirable to include an added permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer® (231, 182, 184), Tween® (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; e.g., U.S. Pat. No. 4,568,343); amides and other nitrogenous compounds such as urea, dimethylacetamide (OMA), dimethylformamide (DMF), 2-pyrrolidone, 1-methyl-2-pyrrolidone, 5 ethanolamine, diethanolamine, and triethanolamine; terpenes; alkanones; and organic acids, particularly citric acid and succinic acid. Azone® and sulfoxides such as DMSO and $C_{10}MSO$ may also be used, but are less preferred.

Most preferred enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter δ of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature.

Anti-seborrhoeic Agents

One or more anti-seborrhoeic active agents known in the art are added to the topical probiotic formulation in certain embodiments. Examples of anti-seborrhoeic active agents include, but are not limited to: certain sulfur-containing amino acids, retinoic acid, 13-cisretinoic acid, cyproterone acetate, benzoyl peroxide, sulfur, vitamin B6 (or pyridoxine), selenium chloride, sea fennel; mixtures of extract of cinnamon, of tea and of octanoylglycine, such as Sepicontrol AS TEA® from Seppic; the mixture of cinnamon, sarcosine and octanoylglycine sold in particular by the company SEPPIC under the trade name Sepicontrol AS®; zinc salts such as zinc gluconate, zinc pyrrolidonecarboxylate (or zinc pidolate), zinc lactate, zinc aspartate, zinc carboxylate, zinc salicylate, zinc cysteate; copper derivatives, and in particular copper pidolate such as Cuivridone® from Solabia; extracts of plants of the species *Arnica montana, Cinchona succirubra, Eugenia caryophyllata, Humulus lupulus, Hypericum*

*perforatum, Mentha piperita, Rosmarinus officinalis, Salvia officinalis*, and *Thymus vulgaris*, all sold, for example, by the company Maruzen; extracts of meadowsweet (*Spiraea ulmaria*) such as the product sold under the name Sebonormine® by the company Silab; extracts of the alga *Laminaria saccharina* such as the product sold under the name Phlorogine® by the company Biotechmarine; mixtures of extracts of salad burnet root (*Sanguisorba officinalis/Poterium officinale*), of ginger rhizomes (*Zingiber officinalis*) and of cinnamon bark (*Cinnamomum cassia*), such as the product sold under the name Sebustop® by the company So labia; linseed extracts, such as the product sold under the name Linumine® by the company Lucas Meyer; Phellodendron extracts, such as those sold under the name Phellodendron extract BG® by the company Maruzen or Oubaku liquid B by the company Ichimaru Pharcos; mixtures of argan oil, of *Serenoa serrulata* (saw palmetto) extract and of sesame seed extract, such as the product sold under the name Regu SEB® by the company Pentapharm; mixtures of extracts of willowherb, of *Terminalia chebula*, of nasturtium and of bioavailable zinc (microalgae), such as the product sold under the name Seborilys® by the company Green Tech; extracts of *Pygeum afrianum*, such as the product sold under the name *Pygeum afrianum* sterolic lipid Extract® by the company Euromed; extracts of *Serenoa serrulata*, such as those sold under the name Viapure Sabal® by the company Actives International, or those sold by the company Euromed; mixtures of extracts of plantain, of *Berberis aquifolium* and of sodium salicylate, such as the product sold under the name Seboclear® by the company Rahn; clove extract, such as the product sold under the name Clove extract Powder® by the company Maruzen; argan oil, such as the product sold under the name Lipofructyl® by Laboratoires Serobiologiques; lactic protein filtrates, such as the product sold under the name Normaseb® by the company Sederma; extracts of the alga Laminaria, such as the product sold under the name Laminarghane® by the company Biotechmarine; oligosaccharides of the alga *Laminaria digitata*, such as the product sold under the name Phycosaccharide AC® by the company Codif; cane sugar extracts, such as the product sold under the name Policosanol ® by the company Sabinsa; sulfonated shale oil, such as the product sold under the name Ichthyol Pale® by the company Ichthyol; extracts of European meadowsweet (*Spiraea ulmaria*), such as the product sold under the name Cytobiol® Ulmaire by the company Libiol; sebacic acid, in particular sold in the form of a sodium polyacrylate gel under the name Sebosoft® by the company Sederma; glucomannans extracted from konjac tuber and modified with alkylsulfonate chains, such as the product sold under the name Biopol Beta® by the company Arch Chemical; extracts of *Sophora angustifolia*, such as those sold under the name Sophora Powder® or Sophora Extract® by the company Bioland; extracts of *Cinchona succirubra* bark, such as the product sold under the name Red bark HS® by the company Alban Muller; extracts of *Quillaja saponaria*, such as the product sold under the name Panama wood HS® by the company Alban Muller; glycine grafted onto an undecylenic chain, such as the product sold under the name Lipacide UG OR® by the company Seppic; the mixture of oleanolic acid and of nordihydroguaiaretic acid, such as the product sold in the form of a gel under the name AC.Net® by the company Sederma; phthalimidoperoxyhexanoic acid; tri($C_{12}$-$C_{13}$) alkyl citrate sold under the name Cosmacol® ECI by the company Sasol; tri($C_{14}$-$C_{15}$) alkyl citrate sold under the name Cosmacol® ECL by the company Sasol; 10-hydroxydecanoic acid, and in particular mixtures of 10-hydroxydecanoic acid, of sebacic acid and of 1,10-decanediol, such as the product sold under the name Acnacidol® BG by the company Vincience; and mixtures thereof.

Skin Hydrating Agents

A hydrating active agent is an active agent capable of reducing the state of dryness of an epidermis. The term "hydrating active agent" is intended to mean: either a compound that acts on the barrier function, with a view to maintaining the hydration of the *stratum corneum*, or an occlusive compound. Mention may be made of ceramides, sphingoid-based compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, pentacyclic triterpenes, petroleum jelly and lanolin; or a compound which directly increases the water content of the *stratum corneum*, such as urea and its derivatives, threalose and its derivatives, hyaluronic acid and its derivatives, glycerol, pentanediol, pidolates, serine, xylitol, lactic acid and sodium lactate, glyceryl polyacrylate, ectoin and its derivatives, chitosan, oligosaccharides and polysaccharides, cyclic carbonates, N-lauroylpyrrolidonecarboxylic acid and N-α-benzoyl-L-arginine; or a compound that activates the sebaceous glands, such as steroidal derivatives (including DHEA), and vitamin D and its derivatives. These compounds may represent from 0.001% to 3% by weight, and preferably from 0.01% to 20% by weight, of the topical formulation.

Skin Conditioning Agents

Other additives include beneficial agents such as those materials that condition the skin (particularly, the upper layers of the skin in the *stratum corneum*) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (vitamin C) and ascorbic acid derivative commonly used in the art (e.g., magnesium ascorbyl phosphate), α-tocopherol (vitamin 10 E), β-tocopherol, γ-tocopherol, δ-tocopherol, ε-tocopherol, $\zeta_1$-tocopherol, $\zeta_2$-tocopherol, η-tocopherol, and retinal (vitamin A), and/or pharmaceutically acceptable salts, esters, amides, or other derivatives thereof. A preferred tocopherol compound is α-tocopherol. Additional agents include those that are capable of improving oxygen supply in skin tissue, as described, for example, in Gross, et al., WO 94/00098 and Gross, et al., WO 94/00109, both assigned to Lancaster Group AG and incorporated herein by reference. Sunscreens may also be included.

Other embodiments may include a variety of non-carcinogenic, non-irritating healing materials that facilitate treatment with the formulations of the invention. Such healing materials may include nutrients, minerals, vitamins, electrolytes, enzymes, herbs, plant extracts, glandular or animal extracts, or safe therapeutic agents that may be added to the formulation to facilitate the healing of dermal disorders.

The amounts of these various additives are those conventionally used in the cosmetics field, and range, for example, from about 0.01% to about 20% by weight of the topical formulation.

The formulations of the invention may also include conventional additives such as opacifiers, fragrance, colorant, stabilizers, surfactants, and the like.

Antimicrobial Agents

In certain embodiments, other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof In some embodiments, the preservatives of the formulations disclosed herein include plant-derived compounds or compound mixtures. In certain embodiments, the plant-derived compounds or compound mixtures are selected from the group consisting of: grapefruit seed extract, radish root ferment filtrate, *Aloe barbadensis* leaf ferment filtrate, *Sorbus aucuparia* fruit ferment filtrate, *Ribes nigrum* (black currant) fruit extract, *Sambucus nigra* fruit extract, japonica root extract, *Zingiber officinale* (ginger) root extract, *Allium sativum* (garlic) bulb extract, *Origanum vulgare* leaf extract, *Thymus vulgaris* (thyme) leaf extract, *Rosmarinus officinalis* (rosemary) leaf extract, and combinations thereof. In preferred embodiments, the topical formulations are paraben-free. In certain embodiments, the preservative component is from about 0.05-15% by weight of the topical formulations disclosed herein. In preferred embodiments, the preservative component is from about 0.1-5.0% by weight of the topical formulations disclosed herein.

Irritation-mitigating Additives

The formulations disclosed herein may also contain irritation-mitigating additives to minimize or eliminate the possibility of skin irritation or skin damage resulting from the chemical entity to be administered, or other components of the composition. Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, may be incorporated into the compositions at a concentration effective to mitigate irritation or skin damage, typically representing not more than about 20 wt. %, more typically not more than about 5 wt. %, of the formulation.

Natural Functional Additives

In certain embodiments, the formulations disclosed herein include one or more functional (e.g., antimicrobial, anti-inflammatory) ingredients derived from natural sources. In some embodiments, one or more natural functional additives are derived from the group consisting of: essential oils, oregano oil, sage oil, lavender oil, rosemary oil, thyme oil, neem oil, lemongrass oil, peppermint oil, eucalyptus oil, tea tree oil, cedar wood oil, carrot seed oil, German Chamomile oil, clove oil, cypress oil, helichrysum oil, myrtle oil, sea buckthorn, Ylang Ylang oil, evening primrose oil, hemp oil, jojoba oil, rosehip seed oil, sesame seed oil, honey, garlic extract, cabbage extract, grapefruit seed extract, raw apple cider vinegar, echinacea, fermented food extracts, lemon juice extract, beer extract, egg extract, soap nut (Reetha), Fuller's earth (multani mitti), orange peel extract, banana extract, Fenugreek seed extract, and *Solanum chrysotrichum* extract.

Botanical Additives

In certain embodiments, the formulations disclosed herein include one or more botanical, or botanical-derived ingredients. In some embodiments, one or more botanicals are derived from the group consisting of: Castanha do Brasil (Brazil nut, *Bertholletia excelsa*) oil and butter, mauritia fruit, essential buriti fruit oil (*Mauritia flexuosa*), andiroba seed oil, mango seed oil and butter, jojoba oil, olive squalane, oil, and leaf extract, sunflower oil, Sangre de Drago, Samambaia, Una de Gato, Camu Camu, cupuacu oil and butter, Espinheira Santa, Maracuja (passion flower) oil, vitamin E, sandelwood essential oil, avocado oil, coconut (*Cocos nucifera*) oil, sweet almond oil, Aloe Vera (*Aloe Barbadensis*) leaf juice, butter, and oil, shea butter, macadamia nut oil, blueberry seed oil, pomegranate seed oil, green tea extract, lemon essential oil, lime essential oil, mandarin oil and butter, tangerine oil and butter, orange blossom, sweet orange oil, orange wild oil, orange essence oil, vanilla extract, guarana extract, palm butter, and wheat proteins. One of skill in the art would readily appreciate that additional botanicals could be used in addition to those disclosed herein.

Miscellaneous Additives

Various other additives may be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence may be pharmaceutically or otherwise desirable. Typical examples of optional additives for inclusion in the formulations of the invention are as follows: sugar substitutes, i.e., artificial sweeteners, (e.g., stevia, aspartame, sucralose, neotame, acesulfame potassium (Ace-K), saccharin, and advantame); caffeine; preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate-60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), α-tocopherol (vitamin 10 E), β-tocopherol, γ-tocopherol, δ-tocopherol, ε-tocopherol, $\zeta_1$-tocopherol, $\zeta_2$-tocopherol, η-tocopherol, and retinal (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that may be obtained commercially under the Carbopol trademark.

Topical Product Application

In an embodiment of the disclosed invention the topical probiotic and/or soluble metabolite component and/or lysate formulation is applied with or without oral administration of a formulation of a probiotic and/or soluble metabolite component and/or lysate. In some embodiments of the invention, the two formulations contain different combinations of active ingredients and/or different concentrations of one or more active ingredients.

In its simplest form, a cream, lotion, gel, ointment, paste, or the like may be spread on the affected surface and gently rubbed in. A solution may be applied in the same way, but more typically will be applied with a dropper, swab, or the like, and carefully applied to the affected areas. The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily.

The probiotic topical formulation can be applied to the scalp as a leave-in conditioning treatment after shampooing. In some embodiments, the conditioning treatment is a water-based liquid that is sprayed onto the scalp. In general, it is contemplated that the formulations of the invention will be applied in the range of once or twice weekly up to once or twice daily. In some embodiments, the topical formulation can be applied to the scalp in the form of a shampoo, or a single combined shampoo and conditioner formulation.

In one application of the topical product, the following methods are used for the treatment of dandruff: (1) Hair is washed by stylist in salon using a mild clarifying shampoo to remove residues on hair and scalp. In one embodiment of the disclosed invention, clarifying of the hair and scalp is carried out in tandem with exfoliation of the scalp. In another embodiment of the disclosed invention, clarifying of the hair and scalp is carried out in tandem with exfoliation of the scalp where an abrasive agent is added to the clarifying shampoo. In yet another embodiment of the disclosed invention, clarifying of the hair and scalp is carried out in tandem with exfoliation of the scalp where an abrasive agent is added to the clarifying shampoo, and the abrasive agent consists of one or more ingredients including but not limited to: coffee grinds in the quantities of 0.1 to 10% by weight; black salt in the quantities of 0.1 to 2% by weight. In some embodiments, either coffee grinds or black salt are used in the disclosed concentrations. In other embodiments, a standard shampoo and/or conditioner are used, or no shampoo is used at this stage. (2) The topical product is applied directly to the scalp by the stylist and allowed to penetrate. (3) The damp hair is blow-dried without rinsing out the topical product. (4) The client is given an at-home version of the topical product along with directions on how to apply it. In one embodiment of the disclosed invention, the at-home topical formulation is different from the in-salon topical formulation. (5) The client applies the at-home topical formulation in a similar fashion to the in-salon treatment. The frequency of application can be from twice daily to once weekly. (6) After a predetermined period of time, the client returns to the salon for a follow-on visit. The time between salon visits can be from once weekly to once every three months. (7) If, after a certain period of time (e.g., one week, or one month, or three months) the topical product the client and stylist may decide to apply a mild antibiotic treatment to the scalp in consultation with a dermatologist. In an embodiment of the invention, the topical antibiotic is one or more from the following commonly used in the art: macrolides, pyranosides and tetracyclines, and erythromycin. (8) Within a predetermined period of time (e.g., one day, one week, or one month) the application of the probiotic topical formulation is repeated.

In various embodiments, the present invention is also directed to a kit with an intended function of facilitating the treatment of dandruff. The kit can be configured in numerous ways to be useful for practicing any of the inventive methods disclosed herein, including the treatment of dandruff with one or more of the inventive formulations, or one or more components thereof, disclosed herein.

The kit is an assemblage of materials or components, including at least one of the inventive formulations, or one or more components thereof. Thus, in some embodiments the kit contains a formulation including one or more probiotic, and/or one or more soluble metabolome component, and/or one or more cell lysate, and/or any of the complementary agents described above, and combinations thereof, administered topically or orally or topically and orally, with or without shampoo, conditioner, or other categories of additional components and/or agents described above and below.

In some embodiments, the kit is configured particularly for use with mammalian subjects. In some embodiments, the kit is configured particularly for use with human subjects.

Instructions for use may be included in the kit. "Instructions for use" typically include a tangible expression describing the technique to be employed in using the components of the kit to affect a desired outcome, including treatment of dandruff with one or more of the formulations, or components thereof, as disclosed herein.

The materials and/or components assembled in the kit can be provided and stored in any convenient and suitable way that preserves their operability and utility. For example, the formulations, or one or more components thereof, can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as one or more of the inventive formulations and the like. The packaging material is constructed by well-known methods, preferably to provide a sterile, contaminant-free environment. As used herein, the term "package" refers to a suitable solid matrix or material such as glass, plastic, paper, foil, Styrofoam and the like, capable of holding the individual kit components. Thus, for example, a package can be a glass, plastic, or paper vessel used to contain suitable quantities of an inventive formulation containing dandruff treatment formulations including: one or more probiotic, and/or one or more soluble metabolome component, and/or one or more cell lysate, and/or any of the complementary agents described above, and combinations thereof, administered topically or orally or topically and orally, with or without shampoo, conditioner, or other categories of additional components and/or agents described above and below. The packaging material generally has an external label which indicates the contents and/or purpose of the kit and/or its components, as well as its various marketable attributes.

In certain embodiments, the implements are selected from the group consisting of: a customized product applicator for convenient at-home application of the product to the scalp, disposable gloves, a brush, a comb, a hand-held blow dryer, combinations thereof, and the like. The kit components preferably are separately packaged and contained in an outer package. The outer package can be a box or carton or shrink wrap, and preferably has instructional indicia printed thereon or visible therethrough.

In various embodiments of the invention, the customized product applicator for convenient at-home application of the product to the scalp includes one or more device from the following groups: (i) Device made of plastic, metal, or combination thereof based on baster used in cooking; (ii) Spring-loaded device made of plastic, metal, or combination thereof based on pipettor used in science research; (iii) Special comb with hollow teeth and hollow handle. The product is filled through the handled and dispensed directly to the scalp through the teeth by applying pressure to the flexible handle. In another embodiment of the invention, the hollow comb is based on designs known in the art (e.g., U.S. Pat. Nos. 6,244,273 and 4,090,522).

EXAMPLES

Example 1

In some embodiments, the formulation for treatment of dandruff is a sugar coated tablet and comprises, consists of or consists essentially of ingredients in Table 1.

TABLE 1 the probiotic formulation may have the following composition:

| Ingredients for sugar coated tablet | mg/Sugar Tablet (unless other units are indicated) |
|---|---|
| L. rhamnosus (lyophilized) | $10^8$-$10^{10}$ CFU |
| L. rhamnosus (lyophilized) | $10^8$-$10^{10}$ CFU |
| Excipient of Sugar Tablet | |
| Microcrystalline cellulose | 70 |
| Encompress ™ | 60 |
| Magnesium stearate | 3 |
| Anhydrous colloidal silica | 1 |
| Coating Agents | |
| Shellac | 5 |
| Talc | 61 |
| Saccharose | 250 |
| Polyvidone | 6 |
| Titanium dioxide | 0.3 |
| Coloring agent | 5 |

Example 2

In some embodiments, the formulation for treatment of dandruff is a scalp lotion and comprises, consists of or consists essentially of ingredients in Table 2.

TABLE 2 the probiotic formulation may have the following

| Ingredient for scalp lotions | Weight % |
|---|---|
| L. rhamnosus (lyophilized) | 1-10 |
| L. rhamnosus (lyophilized) | 1-10 |
| Butyric acid | 0.1-1 |
| D,L-lactic acid | 0.5-5 |
| Glucose | 0.5-5 |
| Glycogen | 0.5-5 |
| Natural functional additive | 0.5-5 |
| Botanical additive | 0.5-5 |
| Preservative | 0.3 |
| Water, purified | |
| Adjust to pH | 3.5 |

Example 3

In some embodiments, the formulation for treatment of dandruff is scalp care milk and comprises, consists of or consists essentially of ingredients in Table 3.

TABLE 3 the probiotic formulation may have the following composition:

| Ingredients for scalp care milk | Weight % |
|---|---|
| L. rhamnosus (lyophilized) | 1-10 |
| L. rhamnosus (lyophilized) | 1-10 |
| Butyric acid | 0.1-1 |
| D,L-lactic acid | 0.5-5 |
| Glucose | 0.5-5 |
| Glycogen | 0.5-5 |
| Natural functional additive | 0.5-5 |
| Botanical additive | 0.5-5 |
| Magnesium ascorbyl phosphate | 0.25-2.5 |
| Sinnowax AO ® (Henkel) | 3.00 |
| Cetyl alcohol | 1.00 |
| Dimethicone | 1.00 |
| Liquid petroleum jelly | 6.00 |
| Isopropyl myristate | 3.00 |
| Glycerol | 20.00 |
| Preservative | 0.3 |
| Water, purified | |
| Adjust to pH 3.5 | |

Example 4

In some embodiments, the formulation for treatment of dandruff is scalp care mousse and comprises, consists of or consists essentially of ingredients in Table 4.

TABLE 4

The probiotic formulation may have the following composition:

| Ingredients of scalp care mousse | Weight % |
|---|---|
| L. rhamnosus (lyophilized) | 1-10 |
| L. rhamnosus (lyophilized) | 1-10 |
| Butyric acid | 0.1-1 |
| D,L-lactic acid | 0.5-5 |
| Glucose | 0.5-5 |
| Glycogen | 0.5-5 |
| Natural functional additive | 0.5-5 |
| Botanical additive | 0.5-5 |
| Magnesium ascorbyl phosphate | 0.25-2.5 |
| Propylene glycol | 0.5-5 |
| Nonionic emulsifying wax | 0.5-5 |
| Quaternium-52 | 0.5-5 |
| Ethanol | 1-40 |
| Propane/butane | 3-20 |
| Preservative | 0.3 |
| Water, purified | |
| Adjust to pH 3.5 | |

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

1. Turnbaugh, P. J.; Ley, R. E.; Hamady, M.; Fraser-Liggett, C. M.; Knight, R.; Gordon, J. I., The Human Microbiome Project. *Nature* 2007, 449, 804-810.
2. Peterson, J.; Garges, S.; Giovanni, M.; McInnes, P.; Wang, L.; Schloss, J. A.; Bonazzi, V.; McEwen, J. E.; Wetterstrand, K. A.; Deal, C.; Baker, C. C.; Di Francesco, V.; Howcroft, T. K.; Karp, R. W.; Lunsford, R. D.; Wellington, C. R.; Belachew, T.; Wright, M.; Giblin, C.; David, H.; Mills, M.; Salomon, R.; Mullins, C.; Akolkar, B.; Begg, L.; Davis, C.; Grandison, L.; Humble, M.; Khalsa, J.; Little, A. R.; Peavy, H.; Pontzer, C.; Portnoy, M.; Sayre, M. H.; Starke-Reed, P.; Zakhari, S.; Read, J.; Watson, B.; Guyer, M.; Grp, N. H. W., The NIH Human Microbiome Project. *Genome Res.* 2009, 19, 2317-2323.
3. Bouslimani, A.; Porto, C.; Rath, C. M.; Wang, M. X.; Guo, Y. R.; Gonzalez, A.; Berg-Lyon, D.; Ackermann, G.; Christensen, G. J. M.; Nakatsuji, T.; Zhang, L. J.; Borkowski, A. W.; Meehan, M. J.; Dorrestein, K.; Gallo, R. L.; Bandeira, N.; Knight, R.; Alexandrov, T.; Dorrestein, P. C., Molecular Cartography of the Human Skin Surface in 3D. *Proc. Nat. Acad. Sci.* 2015, 112, E2120-E2129.
4. Findley, K.; Grice, E. A., The Skin Microbiome: A Focus on Pathogens and Their Association with Skin Disease. *PLoS Pathog.* 2014, 10.
5. Costello, E. K.; Lauber, C. L.; Hamady, M.; Fierer, N.; Gordon, J. I.; Knight, R., Bacterial Community Variation in Human Body Habitats Across Space and Time. *Science* 2009, 326, 1694-1697.
6. Grice, E. A.; Kong, H. H.; Conlan, S.; Deming, C. B.; Davis, J.; Young, A. C.; Bouffard, G. G.; Blakesley, R. W.; Murray, P. R.; Green, E. D.; Turner, M. L.; Segre, J. A.; Nisc Comparative Sequencing Program, Topographical and Temporal Diversity of the Human Skin Microbiome. *Science* 2009, 324, 1190-1192.
7. Nakatsuji, T.; Chiang, H. I.; Jiang, S. B.; Nagarajan, H.; Zengler, K.; Gallo, R. L., The Microbiome Extends to Subepidermal Compartments of Normal Skin. *Nat. Commun.* 2013, 4.
8. Schommer, N. N.; Gallo, R. L., Structure and Function of the Human Skin Microbiome. *Trends Microbiol.* 2013, 21, 660-668.
9. Xu, J.; Saunders, C. W.; Hu, P.; Grant, R. A.; Boekhout, T.; Kuramae, E. E.; Kronstad, J. W.; DeAngelis, Y. M.; Reeder, N. L.; Johnstone, K. R.; Leland, M.; Fieno, A. M.; Begley, W. M.; Sun, Y.; Lacey, M. P.; Chaudhary, T.; Keough, T.; Chu, L.; Sears, R.; Yuan, B.; Dawson, T. L., Dandruff-associated *Malassezia* Genomes Reveal Convergent and Divergent Virulence Traits Shared with Plant and Human Fungal Pathogens. *Proc. Natl. Acad. Sci. U.S.A.* 2007, 104, 18730-18735.
10. Clavaud, C.; Jourdain, R.; Bar-Hen, A.; Tichit, M.; Bouchier, C.; Pouradier, F.; El Rawadi, C.; Guillot, J.; Menard-Szczebara, F.; Breton, L.; Latge, J. P.; Mouyna, I., Dandruff Is Associated with Disequilibrium in the Proportion of the Major Bacterial and Fungal Populations Colonizing the Scalp. *PLoS One* 2013, 8, e58203.
11. Harding, C. R.; Moore, A. E.; Rogers, J. S.; Meldrum, H.; Scott, A. E.; McGlone, F. P., Dandruff: a Condition 12. Gupta, A. K.; Batra, R.; Bluhm, R.; Boekhout, T.; Dawson, T. L., Skin Diseases Associated with *Malassezia* species. *J. Am. Acad. Dermatol.* 2004, 51, 785-798.
13. Reid, G.; Jass, J.; Sebulsky, M. T.; McCormick, J. K., Potential Uses of Probiotics in Clinical Practice. *Clin. Microbiol. Rev.* 2003, 16, 658-+.
14. Soares, R. C.; Zani, M. B.; Arruda, A.; de Arruda, L. H. F.; Paulino, L. C., *Malassezia* Intra-Specific Diversity and Potentially New Species in the Skin Microbiota from Brazilian Healthy Subjects and Seborrheic Dermatitis Patients. *PLoS One* 2015, 10, e0117921.
15. Wang, L. L.; Clavaud, C.; Bar-Hen, A.; Cui, M.; Gao, J.; Liu, Y. Y.; Liu, C.; Shibagaki, N.; Gueniche, A.; Jourdain, R.; Lan, K.; Zhang, C. Y.; Altmeyer, R.; Breton, L., Characterization of the Major Bacterial-fungal Populations Colonizing Dandruff Scalps in Shanghai, China, Shows Microbial Disequilibrium. *Exp. Dermatol.* 2015, 24, 398-400.
16. Hillier, S. L., The Complexity of Microbial Diversity in Bacterial Vaginosis. *N. Engl. J. Med.* 2005, 353, 1886-1887.
17. Fredricks, D. N.; Fiedler, T. L.; Marrazzo, J. M., Molecular Identification of Bacteria Associated with Bacterial Vaginosis. *N. Engl. J. Med.* 2005, 353, 1899-1911.
18. Srinivasan, S.; Liu, C. Z.; Mitchell, C. M.; Fiedler, T. L.; Thomas, K. K.; Agnew, K. J.; Marrazzo, J. M.; Fredricks, D. N., Temporal Variability of Human Vaginal Bacteria and Relationship with Bacterial Vaginosis. *PLoS One* 2010, 5, e10197.
19. Ravel, J.; Gajer, P.; Abdo, Z.; Schneider, G. M.; Koenig, S. S. K.; McCulle, S. L.; Karlebach, S.; Gorle, R.; Russell, J.; Tacket, C. O.; Brotman, R. M.; Davis, C. C.; Ault, K.; Peralta, L.; Forney, L. J., Vaginal Microbiome of Reproductive-age Women. *Proc. Natl. Acad. Sci. U. S. A.* 2011, 108, 4680-4687.
20. Gajer, P.; Brotman, R. M.; Bai, G. Y.; Sakamoto, J.; Schuette, U. M. E.; Zhong, X.; Koenig, S. S. K.; Fu, L.; Ma, Z. S. S.; Zhou, X.; Abdo, Z.; Forney, L. J.; Ravel, J., Temporal Dynamics of the Human Vaginal Microbiota. *Sci. Transl. Med.* 2012, 4, 132ra152.
21. Srinivasan, S.; Hoffman, N. G.; Morgan, M. T.; Matsen, F. A.; Fiedler, T. L.; Hall, R. W.; Ross, F. J.; McCoy, C. O.; Bumgarner, R.; Marrazzo, J. M.; Fredricks, D. N., Bacterial Communities in Women with Bacterial Vaginosis: High Resolution Phylogenetic Analyses Reveal Relationships of Microbiota to Clinical Criteria. *PLoS ONE* 2012, 7, e37818.
22. Rose, W. A., 2nd; McGowin, C. L.; Spagnuolo, R. A.; Eaves-Pyles, T. D.; Popov, V. L.; Pyles, R. B., Commensal Bacteria Modulate Innate Immune Responses of Vaginal Epithelial Cell Multilayer Cultures. *PLoS One* 2012, 7, e32728.

The invention claimed is:

1. A method for reducing dandruff of the scalp in a subject in need thereof, comprising administering to the subject an effective amount of a composition comprising:
   (i) a commensal vaginal *Lactobacillus jensenii* or *Lactobacillus vaginalis* that has undergone less than 6 subcultures following isolation from human clinical vaginal specimens;
   (ii) D,L-lactic acid, L-lactic acid, D-lactic acid, or a combination thereof; and
   (iii) at least one cell lysate component of the *Lactobacillus* spp.,
so as to reduce dandruff in the subject.

2. The method of claim 1, wherein the *Lactobacillus* spp. reduces the growth of *Malassezia* spp.

3. The method of claim 1, wherein the *Lactobacillus* spp. inhibits the growth of *Malassezia* spp.

4. The method of claim 1, wherein the composition further comprises butyric acid.

5. The method of claim 1, wherein the composition is administered orally.

6. The method of claim 1, wherein the composition is administered topically.

7. The method of claim 1, wherein the composition is administered to the subject's skin.

8. The method of claim 1, wherein the composition is administered to the subject's scalp.

9. The method of claim 1, wherein the composition further comprises butyric acid, glucose and glycogen.

10. The method of claim 1, wherein the composition further comprises butyric acid, glucose, glycogen, magnesium ascorbyl phosphate, cetyl alcohol, dimethicone, isopropyl myristate and glycerol.

11. The method of claim 1, wherein the composition further comprises butyric acid, glucose, glycogen, magnesium ascorbyl phosphate, propylene glycol, Quaternium-52 and ethanol.

12. The method of claim 1, wherein the pH of the composition is between 3 and 6.

13. The method of claim 1, further comprising administering one or more anti-seborrhoeic agents.

14. The method of claim 13, wherein the composition and the anti-seborrhoeic agent are administered sequentially.

15. The method of claim 13, wherein the composition and the anti-seborrhoeic agent are administered simultaneously.

* * * * *